(12) United States Patent  (10) Patent No.: US 8,132,712 B2
Fenlon  (45) Date of Patent: Mar. 13, 2012

(54) METERED-DOSE INHALER

(75) Inventor: Derek Fenlon, Waterford (IE)

(73) Assignee: Ivax Pharmaceuticals Ireland, Waterford (IE)

( * ) Notice: Subject to any disclaimer, the term of this patent is extended or adjusted under 35 U.S.C. 154(b) by 159 days.

(21) Appl. No.: 12/532,762

(22) PCT Filed: Apr. 1, 2008

(86) PCT No.: PCT/EP2008/002590
§ 371 (c)(1),
(2), (4) Date: Sep. 23, 2009

(87) PCT Pub. No.: WO2008/119552
PCT Pub. Date: Oct. 9, 2008

(65) Prior Publication Data
US 2010/0078490 A1 Apr. 1, 2010

Related U.S. Application Data

(60) Provisional application No. 60/921,320, filed on Apr. 2, 2007.

(30) Foreign Application Priority Data

Apr. 11, 2007 (GB) ..................... 076999.0

(51) Int. Cl.
G06M 1/04 (2006.01)
A61M 11/00 (2006.01)
(52) U.S. Cl. ................. 235/91 R; 128/200.23

(58) Field of Classification Search .................... 235/91; 128/200.23
See application file for complete search history.

(56) References Cited

U.S. PATENT DOCUMENTS

| 4,445,404 | A | * | 5/1984 | Parker | 81/62 |
| 5,485,971 | A | * | 1/1996 | Nakaya et al. | 242/381.1 |
| 5,489,143 | A | * | 2/1996 | Adachi et al. | 297/411.38 |
| 5,490,749 | A | * | 2/1996 | Arbues | 410/103 |
| 5,794,978 | A | * | 8/1998 | Nishide | 280/806 |
| 6,070,502 | A | * | 6/2000 | Chang | 81/63 |
| 6,175,994 | B1 | * | 1/2001 | Nicoletti | 24/68 SK |
| 6,267,315 | B1 | * | 7/2001 | Blackadder et al. | 242/384 |
| 6,446,627 | B1 | * | 9/2002 | Bowman et al. | 128/200.23 |
| 7,252,065 | B1 | * | 8/2007 | Keeton | 123/185.14 |
| 2011/0220450 | A1 | * | 9/2011 | Chiang | 192/64 |

FOREIGN PATENT DOCUMENTS

WO WO 98/28033 A 7/1998
WO WO 2005/114563 A 12/2005

OTHER PUBLICATIONS

International Search Report dated Jul. 10, 2008, application No. PCT/EP2008/002590.

* cited by examiner

Primary Examiner — Daniel Hess
(74) Attorney, Agent, or Firm — RatnerPrestia

(57) ABSTRACT

A metered dose inhaler dose counter, the counter includes: an actuator; a rotary gear wheel having a plurality of ratchet teeth; a driver for driving the rotary gear in a step-wise fashion in response to displacement of the actuator; a pawl that prevents reverse rotation of the rotary gear; and a display coupled to the rotary gear.

19 Claims, 8 Drawing Sheets

METERED-DOSE INHALER

CROSS-REFERENCE TO RELATED APPLICATIONS

This application is the U.S. national phase application of PCT International Application No. PCT/EP2008/002590, filed Apr. 1, 2008, which claims priority to U.S. Provisional Patent Application No. 60/921,320, filed Apr. 2, 2007, and GB Application No. 0706999.0, filed Apr. 11, 2007, the contents of such applications being incorporated by reference herein.

FIELD OF THE INVENTION

This invention relates to a metered-dose inhaler and in particular to a dose counter for a metered-dose inhaler, the counter comprising: an actuator; a rotary gear; a driver for driving the rotary gear in a step-wise fashion in response to displacement of the actuator, the rotary gear comprising a wheel mounted on a spindle which wheel having a plurality of ratchet teeth around its periphery; a pawl to prevent reverse rotation of the rotary gear; and a display coupled to the rotary gear, the display having a visible array of incrementing integers on a surface thereof indexable by a single integer in response to each step of the step-wise rotary motion of the rotary gear; wherein the pawl comprises at least two ratchet teeth which are radially spaced such that one of the teeth engages with the ratchet teeth of the wheel following each step of the step-wise rotary motion of the rotary gear.

BACKGROUND OF THE INVENTION

Metered-dose inhalers include pressurised metered-dose inhalers (of both manually operable and breath-actuated types) and dry-powder inhalers. Such metered-dose inhalers typically comprise a medicament-containing vessel and an actuator body having a drug delivery outlet.

The medicament-containing vessel may be a pressurised canister containing a mixture of active drug and propellant. Such canisters are usually formed from a deep-drawn aluminium cup having a crimped lid which carries a metering valve assembly. The metering valve assembly is provided with a protruding valve stem which, in use, is inserted as a tight push fit into a so-called "stem block" in the actuator body.

To actuate the conventional manually operable inhaler, the user applies a compressive force to the closed end of the canister. The internal components of the metering valve assembly are spring loaded so that a compressive force of about 15 to 30 N is required to activate the device.

In response to this compressive force, the canister moves axially with respect to the valve stem by an amount varying from about 2 to 4 mm. This degree of axial movement is sufficient to actuate the metering valve and cause a metered quantity of the drug and propellant to be expelled through the valve stem. This is then released into the mouthpiece via a nozzle in the stem block. A user inhaling through the drug delivery outlet of the device at this point will thus receive a dose of the drug.

Metered-dose inhalers as described above administer an accurate dose of medicament whenever required, which is particularly useful for users whose respiratory difficulties manifest themselves suddenly. Such has been the success of these devices that they are now used throughout the world.

A more recent development is the so-called "breath-operated actuator" which delivers a dose of drug through a mouthpiece in response to inhalation by the user. This type of arrangement is particularly convenient in circumstances where the co-ordination between user inhalation and manual depression of the aerosol canister is imperfect. For example, children sometimes lack the necessary co-ordination to achieve effective self-administration and, at times of respiratory distress, adult users may also experience poor co-ordination.

SUMMARY OF THE INVENTION

One of the drawbacks of self-administration from an inhaler is that users often experience difficulty in determining when the charge in the medicament-containing vessel has nearly run out since the contents of the medicament reservoir are typically invisible to the user. With aerosol canisters, part of the reason for this difficulty is that a surplus of propellant may remain in the canister even though the drug supply is nearly exhausted. Alternatively, the near-exhausted state may result in a surplus of drug in relation to propellant. Thus, the illusion is created that the inhaler is still capable of providing useful doses of medicament simply because the canister contains liquid. This is potentially hazardous for the user since dosing becomes unreliable and because few users routinely carry a back-up device.

Many users have several different inhalers for the treatment of a variety of conditions. Others keep inhalers at a number of different locations such as at school, home, work etc. In these circumstances it is particularly difficult for the user to keep track of the amount of usage extracted from each individual inhaler apparatus.

Clearly there is a need for a counter mechanism which enables users to assess how many doses remain in the obscured canister. Such a counter would ensure that users are warned when the inhaler nears exhaustion so that appropriate measures can be taken to avoid running out of medication. Moreover, if a dose counter can provide readability to a resolution of one dose, this can be used for compliance monitoring, either under hospital supervision or by parents and teachers assessing compliance by children in their care. In addition, there are regulatory requirements for metered-dose inhalers to have a dose counter in a number of countries.

WO 98/28033 discloses a dose counter suitable for use with the above-described metered-dose inhalers. FIGS. 1 and 2 reproduced herein from WO 98/28033 show the lower portion of a metered-dose inhaler. The inhaler comprises an actuator body 2 having a drug delivery outlet 4. An aerosol canister 6 extends into the lower portion of the actuator 2. The aerosol canister 6 is formed from a deep-drawn aluminium cup 8 to which a lid 10 is attached by crimping.

The lid 10 carries a metering-valve assembly having a protruding valve stem 12, the end of which is received as a tight push fit in a stem block 14 of the actuator body 2. Stem block 14 has a nozzle 16 communicating with the drug delivery outlet 4 so that, upon actuation of the metering-valve assembly, a charge of the drug is emitted through the nozzle 16 into the drug delivery outlet 4. Actuation of the metering-valve assembly is effected by causing downward movement of the aerosol canister 6 relative to the actuator body 2. This may be achieved through manual pressure exerted by the user against the upturned base (not shown) of the aerosol canister 6 or by automatic depression of the aerosol canister 6 in response to user inhalation in inhalers of the breath-actuated type. The mechanism of breath actuation does not form part of WO 98/28033 or the present invention and will not be described in further detail. A user inhaling through the drug delivery outlet 4 when the aerosol canister 6 is depressed will receive a metered dose of the drug.

A counter mechanism 18 includes an actuator 20 moulded from a plastics material, such as nylon, the actuator 20 having a boss 22 integrally formed at its base.

The underside of boss 22 is formed with a blind hole which receives a compression spring 24 mounted on an upstanding spigot 26 formed on a lower element of the counter chassis.

A driver 28 for driving a rotary gear in the form of a ratchet-toothed wheel 30 is integrally moulded with boss 22 of the actuator 20 and comprises a transverse hook element (not shown) mounted between two arms (only one visible in FIG. 2), the bases of which are conjoined to the boss 22. The transverse hook is dimensioned and oriented to engage with ratchet teeth 32 formed around the periphery of the ratchet-toothed wheel 30 to rotate it in a forward direction.

The ratchet-toothed wheel 30 is integrally moulded with a first hollow axle 34 which is rotatably supported on a first spindle 36 that projects transversely from a chassis sub-element 38. Chassis sub-element 38 also has a second spindle 40 projecting transversely therefrom on which a second hollow axle 42 is rotatably supported. A flexible tape 44 is wound around the second hollow axle 42 which serves as a supply spool and passes to the first hollow axle 34 which serves as a take-up spool (stock bobbin). A guide plate 46 forming part of the chassis sub-element 38 helps to guide the tape 44 in a smooth passage from the supply spool to the take-up spool. The surface of the tape 44 is marked with a progression of descending numbers which denote the number of doses remaining in the aerosol canister. Typically, the starting count is 200 and successive markings on the tape decrease by one. The spacing between successive markings is coincident with the indexing motion of the matching wheel 30 so that a new number appears in a window 48 provided in the inhaler housing 2 for each successive actuation.

The ratchet-toothed wheel 30 and integrally formed first hollow axle 34 are restrained from reverse rotation by a wrap-spring clutch 50 surrounding the hollow axle 34 at the end thereof remote from ratchet-toothed wheel 30. One end (not shown) of the wrap-spring clutch 50 is braced against the counter chassis. The windings of the wrap-spring clutch 50 are oriented such that rotation of the first hollow axle 34 in a forward sense is not resisted by the spring coils. However, reverse rotation of the hollow axle 34 acts so as to tighten the spring coils around it, thereby causing the first hollow axle 34 to be gripped by the internal surface of the wrap-spring clutch 50 and hence restraint from reverse rotation.

FIG. 3 shows a preferred embodiment of the invention set out in WO 98/28033. The dose counter 18 comprises an actuator 20 having a boss 22 integrally formed therewith and driver 28 joined to the boss 22. The underside of boss 22 is provided with a blind hole which receives a compression spring 24 that serves to return the actuator 20 to its rest position after depression thereof during actuation of the inhaler apparatus (not shown).

The driver 28 comprises a transverse hook 52 mounted between a pair of arms 54,56 which are joined at their bases by a web (not shown). The web is connected to the boss 22 of the actuator 20. A combined actuator and driver assembly may be integrally formed, such as from a plastics material, e.g. as nylon.

In use, the transverse hook 52 engages with ratchet teeth 32 of a ratchet-toothed wheel 30 which is mounted on a hollow axle 34 serving as a take-up spool for a flexible tape display 44. At the end of the hollow axle 34 remote from the ratchet-toothed wheel 30 is a friction clutch 50 which serves to restrain the axle 34 against reverse rotation and hence prevents reverse travel of the counter tape 44.

A control surface 58 is depicted here as a see-through element so that the workings of the dose counter may be more clearly seen. The control surface 58 extends parallel to the direction of travel of the actuator 20 and is located adjacent the ratchet-toothed wheel 30 at a position which marks a chordal projection across one of the wheel faces. One of the support arms 56 of the driver 28 is in sliding contact with control surface 58. This sliding contact serves to inhibit the natural tendency of the driver 28 to flex radially inwardly towards the axis of rotation of the ratchet-toothed wheel 30. By preventing such radially inward flexure, the control surface 58 restricts the engagement and disengagement of the drive 28 with the ratchet-toothed wheel 30 so that the distance by which the ratchet-toothed wheel 30 rotates is limited to one tooth pitch. This condition is observed regardless of the extent of linear travel, or stroke, of the actuator 20.

FIG. 4 shows a schematic view of a conventional ratchet gear and drive pawl arrangement which is used in the dose counter described in WO 98/28033. The arrangement uses a reciprocating driver 28 acting in a pushing sense to rotate a ratchet-toothed wheel 30 in the direction shown by the arrows A. A fixed pawl 60 acts to prevent reverse rotation of the ratchet-toothed wheel 30 by engagement against the trailing edge 62 of a ratchet tooth 32. However, on forward rotation of the ratchet-toothed wheel 30 in the sense of arrows A, the fixed pawl 60 is capable of radially outward deformation, urged by the leading edge 63 of a ratchet-tooth 32.

In this arrangement, if the ratchet-toothed wheel 30 is rotated by more than a single tooth pitch but by less than two tooth pitches for each reciprocating movement of the driver 28, there is a degree of reverse rotation until the pawl 60 becomes engaged by the trailing edge 62 (as opposed to the leading edge 63) of a ratchet tooth 32. Thus, the rotation of the ratchet-toothed wheel 30 may be said to be "stepped".

The components of metered-dose inhalers are manufactured to a high technical specification. However, inevitable variations in the tolerances of the components can, in some circumstances, lead to failure of the dose counter of the type disclosed in WO 98/28033. The failure of the dose counter, although not common, makes the dose counter of the type disclosed in WO 98/28033 unsuitable for some applications. There is a requirement in the art, therefore, for a dose counter with a reduced failure rate.

Accordingly, a first aspect of the present invention provides a dose counter for a metered-dose inhaler, the counter comprising:

an actuator;
a rotary gear;
a driver for driving the rotary gear in a step-wise fashion in response to displacement of the actuator, the rotary gear comprising a wheel mounted on a spindle which wheel having a plurality of ratchet teeth around its periphery;
a pawl to prevent reverse rotation of the rotary gear; and
a display coupled to the rotary gear, the display having a visible array of incrementing integers on a surface thereof indexable by a single integer in response to each step of the step-wise rotary motion of the rotary gear;
wherein the pawl comprises at least two ratchet teeth which are radially spaced such that one of the teeth engages with the ratchet teeth of the wheel following each step of the step-wise rotary motion of the rotary gear.

The counter of the present invention thus provides a pawl having at least two teeth in which one and the same tooth engages with successive ratchet teeth of the wheel during the step-wise rotary motion of the wheel to prevent reverse rotation of the wheel (and hence the rotary gear). By providing alternative positions for engaging the ratchet teeth of the wheel, the pawl increases the range of tolerances in the manufacture of the various components of the inhaler which can be accommodated. This in turn significantly reduces the failure rate of the dose counter and, in particular, the likelihood of undercounting. Clearly, undercounting is particularly undesirable as it can lead to a patient believing that there are more doses left within the inhaler than there actually are.

BRIEF DESCRIPTION OF THE DRAWINGS

The present invention will now be described with reference to the accompanying drawings, in which.

DETAILED DESCRIPTION OF THE INVENTION

Figure 1:
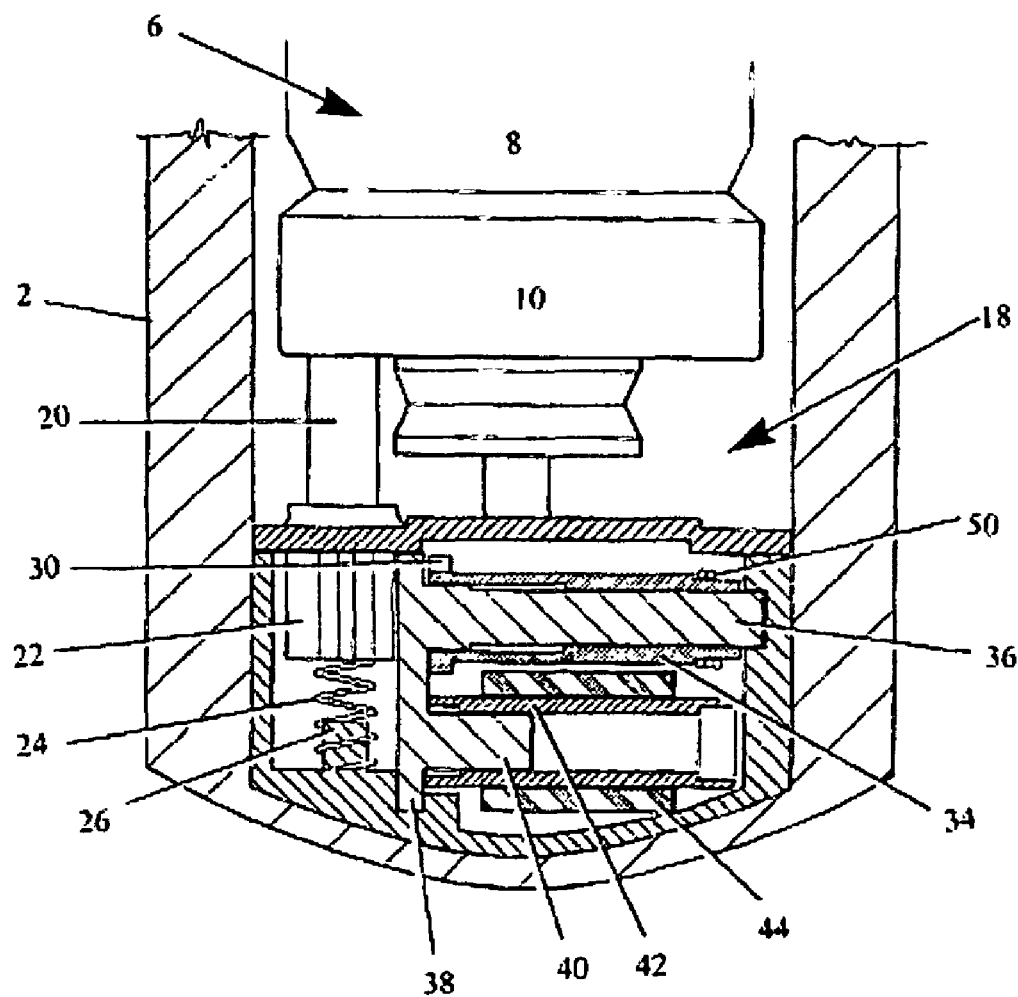
FIGS. 1 to 4 show a dose counter for a metered-dose inhaler according to the prior art document WO 98/28033.
Figure 2:
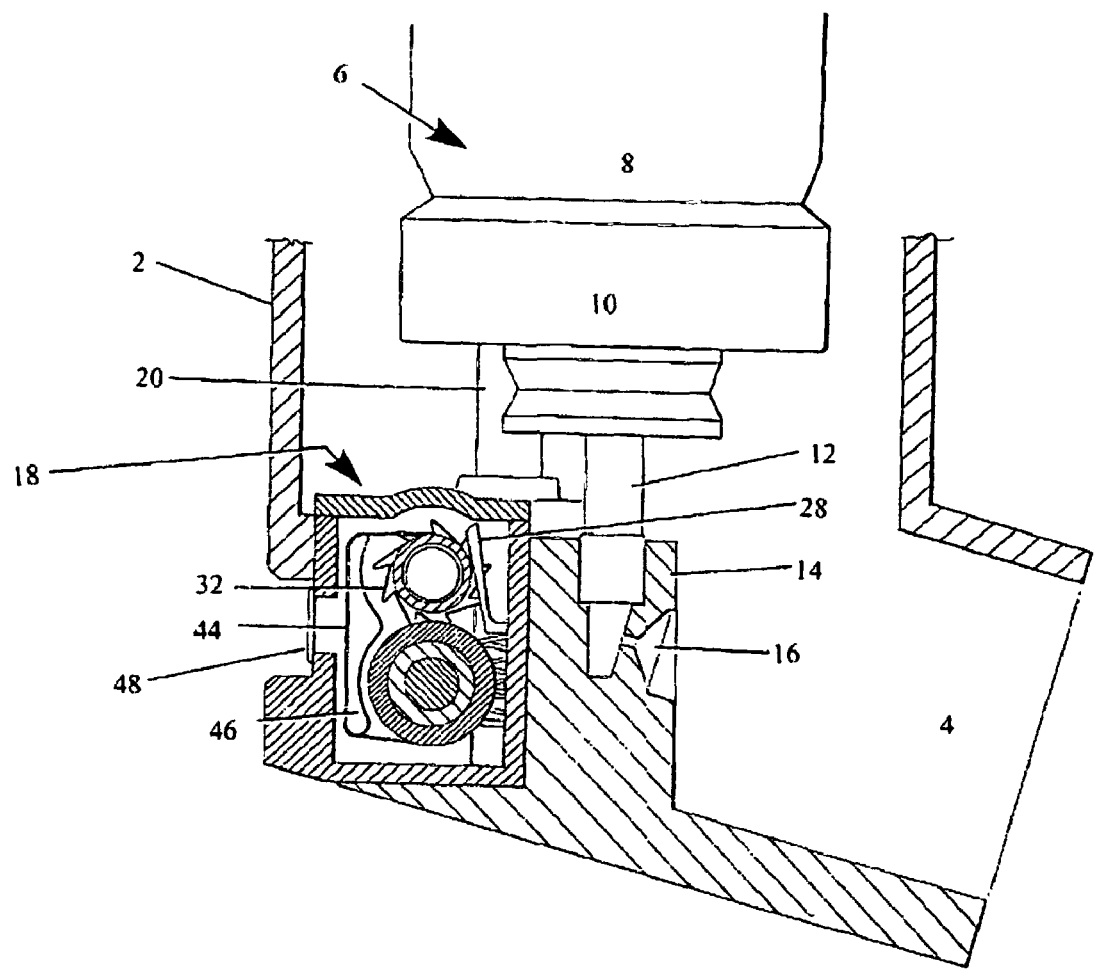
Figure 3:
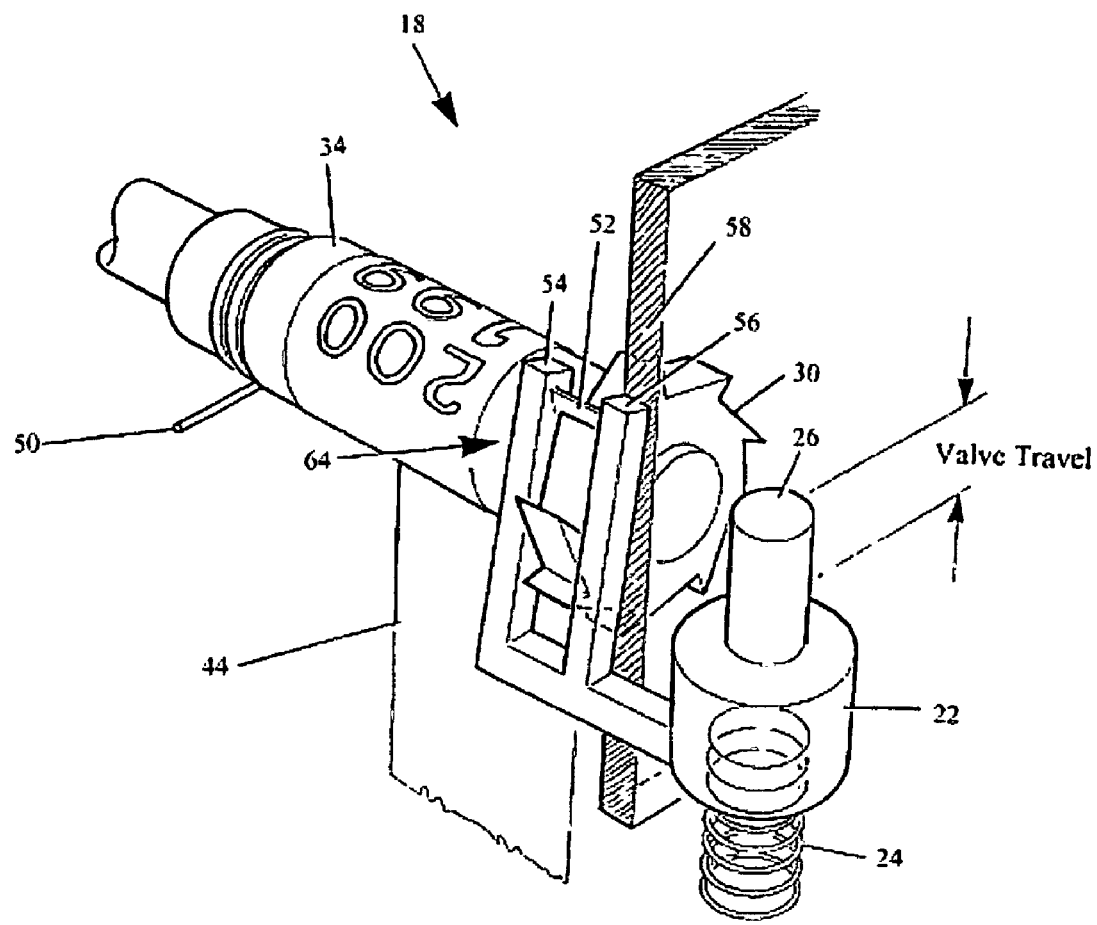
Figure 4:
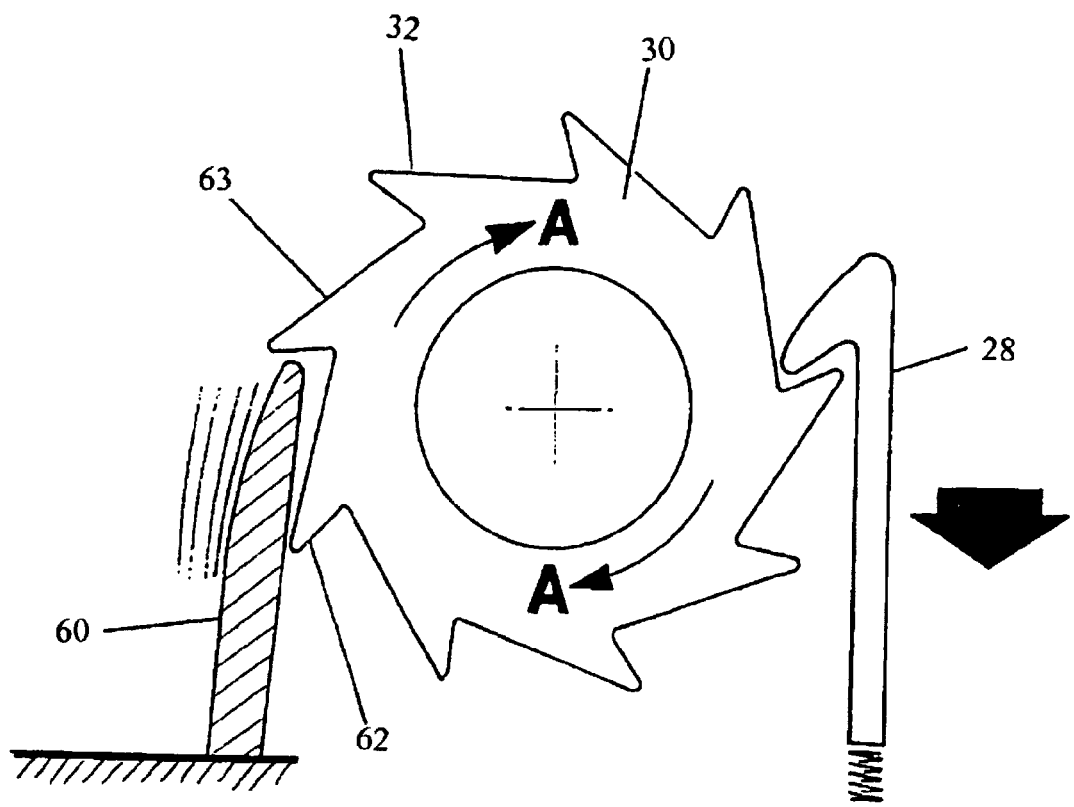
Figure 5:
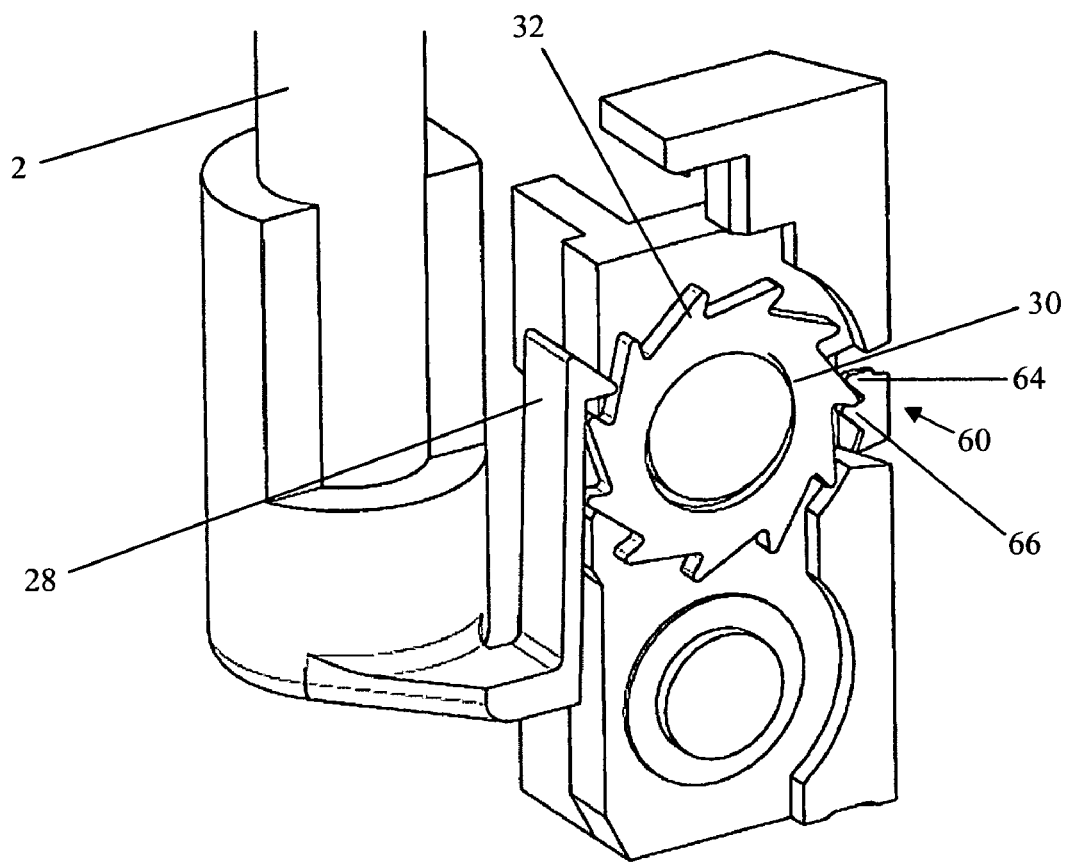
FIG. 5 shows elements of a dose counter according to the present invention.

The dose counter of the present invention is based on that set out in FIGS. 3 and 4 described hereinabove except that the pawl 60 has been modified. Modification of the pawl followed an in-depth study of all of the components of the inhaler. Thus, as shown in FIG. 5, the dose counter 18 of the present invention comprises an actuator 20; a rotary gear (not shown in full in FIG. 5); a driver 28 for driving the rotary gear in a step-wise fashion in response to displacement of the actuator 20, the rotary gear comprising a wheel 30 mounted on a spindle (not shown), the wheel 30 having a plurality of ratchet teeth 32 around its periphery; a pawl 60 to prevent reverse rotation of the rotary gear; and a display (not shown) coupled to the rotary gear, the display having a visible array of incrementing integers on a surface thereof indexable by a single integer in response to each step of the step-wise rotary motion of the rotary gear.

The wheel 30 has a plurality of ratchet teeth 32 and preferably has 8-14 teeth (i.e. 8, 9, 10, 11, 12, 13 or 14), more preferably 9, 10, 11 or 12 teeth, and most preferably 11 teeth.

The radius of the wheel 30 measured from the centre of the wheel 30 to the tip of the teeth 32 will depend on the size of the components of the inhaler. Preferably the radius is from 1.5 to 3.5 mm, more preferably from 2.0 to 3.0 mm and most preferably 2.80±0.05 mm.

As in the dose counter 18 of WO 98/28033, the dose counter 18 of the present invention preferably further comprises a control surface to regulate the position of engagement and disengagement between the driver 28 and the wheel 30. In addition, the driver 28 comprises a ratchet drive pawl and preferably the ratchet drive pawl is in the form of a straddle drive in which the element that engages the ratchet teeth of the wheel is supported between a pair of spaced apart support arms.

The pawl 60 comprises at least two ratchet teeth 64,66. Preferably, as shown in FIG. 5, the pawl 60 comprises two ratchet teeth 64,66 and no more. The at least two ratchet teeth 64,66 are radially spaced with respect to the ratchet-toothed wheel 30 such that one and the same tooth engages with the ratchet teeth 32 of the wheel following each step of the step-wise rotary motion of the rotary gear. Typically, one, and only one, of the ratchet teeth 64,66 on pawl 60 ever engages with the ratchet wheel.

Figure 6:
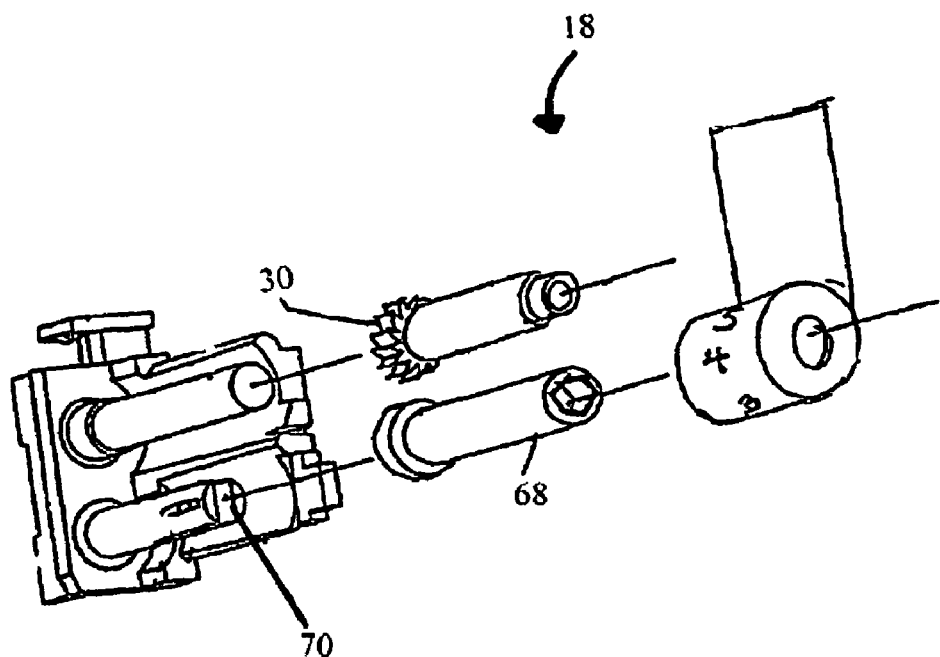
FIG. 6 shows further detail of the dose counter according to the present invention.

FIG. 6 shows an exploded view of the dose counter 18 showing in addition to the previously described components, the stock bobbin 68 which is held taut by the action of the split hub 70. The split hub 70 avoids the need for a clutch spring as set out in WO 98/28033. Although the clutch spring could be used as an alternative or in addition to the split hub 70, in a preferred embodiment, the dose counter of the present invention does not include a clutch spring. The display is preferably an elongate counter tape 44 on which the dose count is printed or written, and more preferably the counter tape 44 is located on an indexing spool and the dose counter further comprises a stock bobbin to receive the counter tape as the indexing spool is advanced in a step-wise fashion.

In use, the operation of the dose counter 18 is as follows.

The user depresses the aerosol canister 6 which causes displacement of the actuator 20. In this embodiment, the actuator 20 is adapted to engage with the rim of the medicament canister 6. The actuator 20 is operable by linear displacement from a first position to a second position and back to the first position and movement of the rotary gear occurs either during the displacement of the actuator from the first position to the second position or during the displacement of the actuator from the second position to the first position. In the embodiment shown in FIG. 5, the movement of the rotary gear occurs during the displacement of the actuator from the first position to the second position. In the embodiment shown, the actuator 20 comprises a spring-loaded plunger 22,24, the plunger being depressible against the return force of the spring loading when the actuator is caused to deliver a dose of medicament.

During the movement from the first position to the second position, the actuator 20 causes the driver 28 to engage the trailing edge 62 of the ratchet tooth 32 of the wheel 30. As the actuator 20 and driver 28 move down the ratchet-toothed wheel 30 rotates.

The spindle of the rotary gear moves the counter tape 44 revealing the next integer. The counter tape 44 is held taut by the action of the split hub 70 on which is mounted the stock bobbin 68.

The pawl 60 radially outwardly deforms to allow the wheel 30 to rotate by one tooth 32. The at least two teeth 64,66 of pawl 60 may be inherently resilient to allow the required radially outward deformation and return. Alternatively or in addition, the pawl 60 may be mounted on a resilient support capable of radially outward deformation, for example the resilient support may be a resilient flange incorporated in to the chassis of the dose counter 18.

The driver 28 releases the ratchet-toothed wheel 30 after it has engaged with the pawl 60. On reset of the inhaler, the canister 6 is allowed to return to its initial (first) position. The compression spring 24 pushes the actuator 20 to follow the canister. The driver 28 on the actuator 20 flexes to pass over the teeth of the ratchet-toothed wheel 30 as the actuator 20 moves from the first to the second position.

The tooth of the at least two teeth 64,66 which has engaged tooth 32 of the wheel 30 prevents the rotary gear from rotating backwards.

The counter mechanism of the type described with reference to WO 98/28033 and in accordance with the present invention must rotate the wheel 30 of the rotary gear by exactly one tooth spacing each time the actuator is depressed. By tooth spacing is meant one tooth pitch, i.e. the radial distance between the same notional point two adjacent teeth 32 on the ratchet-toothed wheel 30. The stroke available for indexing the rotary gear is equal to the full stroke of the actuator 2. Where the metered-dose inhaler is a pressurised inhaler, the stroke available for counting is equal to the full stroke of the medicament canister 6. However, there are three movements (or "journeys") that must be completed within this total distance for indexing of the dose counter to occur. The three journeys are shown schematically in FIG. 7.

Figure 7:
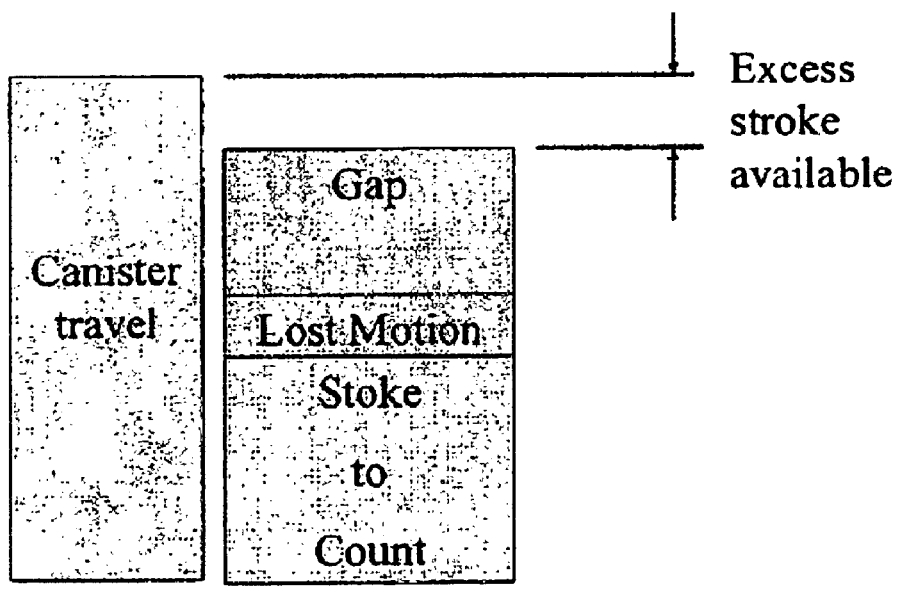
FIG. 7 shows a schematic representation of journeys undertaken for indexing of the dose counter to occur.

FIG. 7 shows a graphical representation the amount of canister travel and the excess stroke available before the three critical journeys must occur. Firstly, the canister travel must close the start gap which is the sum of the tolerances of the manufactured components in the vertical direction. Secondly, the stroke must take up any lost motion, such as in pivot play, flexing of the pawl and arc motion of the drive pawl. Thirdly, is the so-called "stroke to count", which is the journey which leads to indexing of the rotary gear by one tooth spacing.

The stroke available for counting will clearly depend on the type of metered-dose inhaler used. By way of example, a suitable inhaler is the pressurised metered-dosed inhaler EasiBreathe® which uses a Qvar® canister. The canister stroke in this inhaler was measured as 3.04±0.255 mm. This tolerance represents ±3 standard deviations so that 99.7% of all canister strokes will lie within these limits. The measurements were taken from force versus displacement profiles for Qvar® canisters. One hundred and fifty canisters were measured at the start, middle and end of life giving a total of 450 stroke measurements.

The start gap is the tolerance stack in the vertical direction and includes a first distance between the part of the driver 28 which engages the wheel 30 and the appropriate ratchet tooth 32 of the wheel 30 of the rotary gear, and a second distance between the top of the actuator 20 and the canister 6. The tolerance in the vertical direction was found to be ±0.47 mm. The nominal start gap for the EasiBreathe® inhaler is set at 0.85 mm and hence the start gap with tolerances is 0.85±0.47 mm.

Thus, since the start gap is 0.85±0.47 mm the maximum start gap (mean plus 3 standard deviations) is 1.32 mm (0.85±0.47). When such a start gap occurs, a short-stroking canister (for example, 2.79 mm) will not rotate the wheel 30 of the rotary gear by a full tooth spacing. This will lead to failure of the dose counter. However, the provision of a first and second ratchet tooth 64,66 in the pawl 60 allows the ratchet tooth 32 of the wheel 30 of the rotary gear to rest on the second tooth 66. In the present embodiment, the second tooth 66 is 0.60 mm away from the first tooth 64. Thus, for the next actuation, the start gap is reduced to 0.72 mm (1.32−0.60). The stroke is therefore sufficient to rotate the wheel 30 a full index starting from this point. The step-wise rotation of the wheel 30 then continues with all subsequent actuations starting and finishing with the ratchet teeth 32 of the wheel 30 of the rotary gear engaged with the second tooth 66 of the pawl 60.

Figure 8:
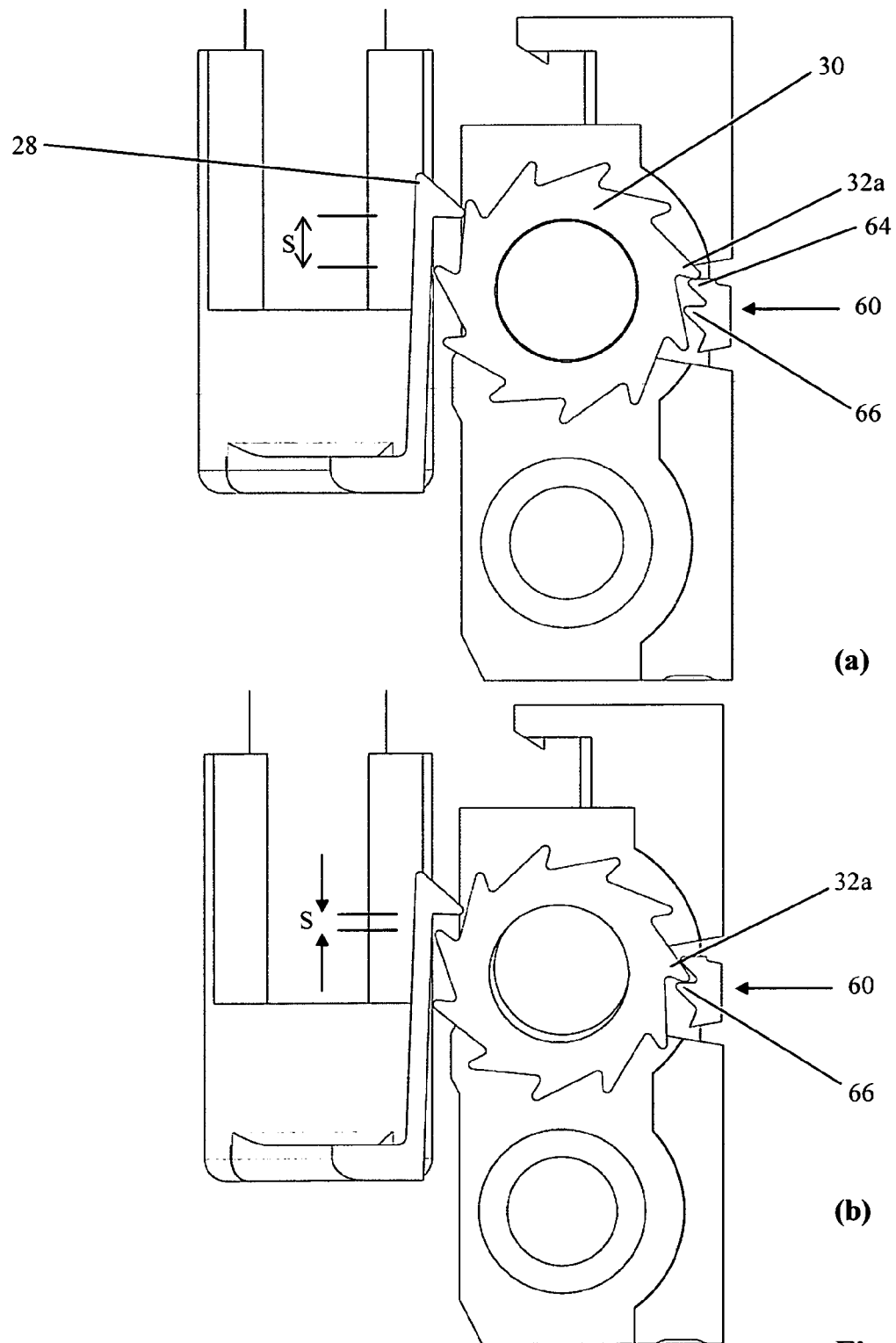
FIG. 8 shows the wheel and pawl of the dose counter of the present invention in which the pawl is (a) operating from the first tooth and (b) operating from the second tooth.

FIG. 8 shows a more detailed view of the wheel 30 of the rotary gear, the driver 28 and the pawl 60 to prevent reverse rotation of the rotary gear. In FIG. 8(a) the ratchet tooth 32a of the wheel 30 is engaged with the first ratchet tooth 64 of the pawl. In FIG. 8(b) the same tooth 32a of the wheel 30 is engaged with the second ratchet tooth 66 of the pawl 60. It may be seen that the start gap is reduced in the arrangement shown in FIG. 8(b) in comparison with the same distance in FIG. 8(a). The second tooth 66 of the pawl 60 therefore allows the first distance S of the start gap (the between the part of the driver 28 which engages the wheel 30 and the appropriate ratchet tooth 32 of the wheel 30) to be reduced thereby accommodating a greater tolerance in the canister stroke.

As explained hereinabove, the first and second teeth 64,66 provide different starting positions for the wheel 30 of the rotary gear to accommodate different tolerance levels in the components of the inhaler. The teeth 64,66 are therefore separated radially with respect to the wheel 30. The spacing will clearly depend on the precise nature of the components used in the inhaler and hence it would be inappropriate to provide a precise numerical value. It is clear from the mechanism, however, that the radial spacing will be less than the radial distance between adjacent teeth 32 on the wheel 30 of the rotary gear.

In the embodiments shown herein, the dose counter 18 of the present invention incorporates a pawl 60 having two teeth 64,66 and only two teeth, i.e. the pawl 60 consists essentially of two teeth 64,66. However, additional teeth could be incorporated to provide additional precision to the start position of the wheel 30 and thus additional precision in the first distance S. For example, the pawl may have 2-6, preferably two, three or four teeth, more preferably two or three and most preferably two teeth.

In a particularly preferred embodiment of the present invention, the dose counter is adapted for a canister stroke of 3.041±0.256 mm: the wheel of the rotary gear has a radius of 2.80±0.05 mm defined as the distance from the centre of the wheel to the tip of the teeth and 11 ratchet teeth around its periphery; and the pawl comprises two ratchet teeth only which have a radial spacing of 0.6 mm. In this embodiment, the total stroke to guarantee a count is 2.372±0.115 mm. The probability of failure to count or resent due to component dimension variations (manufacturing tolerances) is less than 1 in 10 million.

Figure 9:
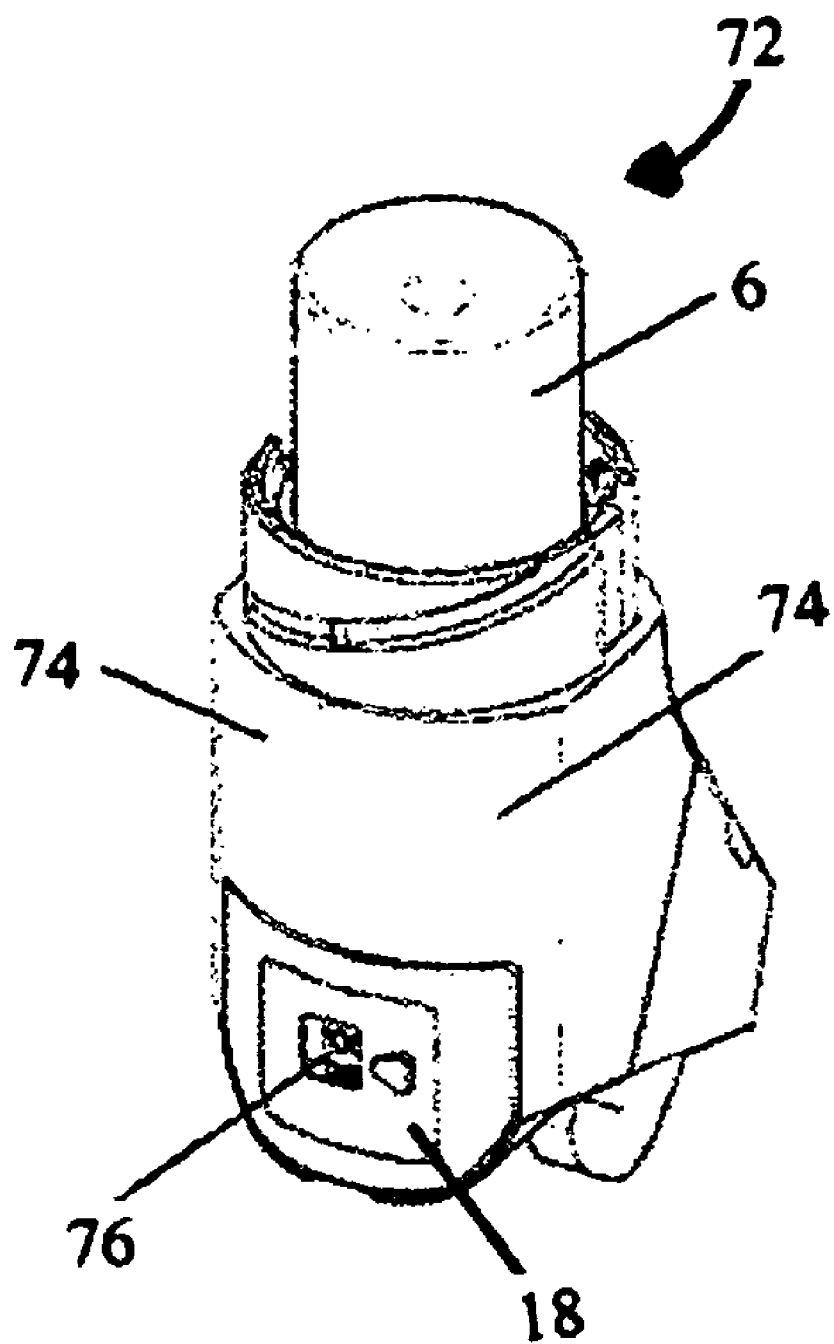
FIG. 9 shows a metered-dose inhaler containing the dose counter of the present invention.

The present invention further provides a metered dose inhaler 72 as shown in FIG. 9. The inhaler comprises a medicament canister 6, an actuator body 74 for receiving the canister 6 and having a medicament delivery outlet, and the dose counter as described herein. The inhaler has a window 76 for viewing the integers on the tape 44. In a preferred embodiment the actuator body 74 comprises a sump and preferably a smooth rounded sump. Typically, a rounded sump is understood to have a substantially cylindrical upper portion and a substantially hemi-spherical lower portion. Typically, smooth is understood to mean that the surface is sufficiently free of surface protrusions to the extent that during normal use medicament will not substantially adhere thereto.

In one embodiment of the invention the vessel contains a medicament in the form of an aerosol. Alternatively in another embodiment of the invention the vessel contains a medicament in the form of a dry powder.

The medicament may be any medicament that is suitable to be delivered to a patient via a metered-dose inhaler. In particular medicaments for the treatment of a wide variety of respiratory disorders are delivered in this manner including anti-allergic agents (e.g. cromoglycate, ketotifen and nedocromil), anti-inflammatory steroids (e.g. beclomethasone dipropionate, fluticasone, budesonide, flunisolide, ciclesonide, triamcinolone acetonide and mometasone furoate); bronchodilators such as: $\beta_2$-agonists (e.g. fenoterol, formoterol, pirbuterol, reproterol, salbutamol, salmeterol and terbutaline), non-selective β-stimulants (e.g. isoprenaline), and xanthine bronchodilators (e.g. theophylline, aminophylline and choline theophyllinate); and anticholinergic agents (e.g. ipratropium bromide, oxitropium bromide and tiotropium).

A further aspect of the present invention provides the use of a pawl 60 comprising at least two ratchet teeth 64,66 for preventing miscounting in a dose counter of a metered dose inhaler 72. A still further aspect of the present invention provides the use of a pawl 60 comprising at least two ratchet teeth 64,66 for preventing undercounting in a counter of a metered dose inhaler 72.

In a preferred embodiment the counter comprises an actuator 20; a rotary gear; a driver 28 for driving the rotary gear in a step-wise fashion in response to displacement of the actuator 20, the rotary gear comprising a wheel 30 mounted on a spindle 36 which wheel 30 having a plurality of ratchet teeth 32 around its periphery; and a display 44 coupled to the rotary gear, the display having a visible array of incrementing integers on a surface thereof indexable by a single integer in response to each step of the step-wise rotary motion of the rotary gear. Preferably, the pawl 60 prevents reverse rotation of the rotary gear.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A dose counter for a metered-dose inhaler, the counter comprising: an actuator; a rotary gear; a driver for driving the rotary gear in a step-wise fashion in response to displacement of the actuator, the rotary gear comprising a wheel mounted on a spindle which wheel having a plurality of ratchet teeth around its periphery; a pawl to prevent reverse rotation of the rotary gear; and a display coupled to the rotary gear, the display having a visible array of incrementing integers on a surface thereof indexable by a single integer in response to each step of the step-wise rotary motion of the rotary gear; wherein the pawl comprises at least two ratchet teeth each for engaging with the ratchet teeth of the wheel to prevent reverse rotation of the rotary gear, the at least two ratchet teeth being radially spaced such that one of the at least two ratchet teeth of the pawl engages with the ratchet teeth of the wheel following each step of the step-wise rotary motion of the rotary gear.

2. A dose counter as claimed in claim 1, wherein the pawl comprises two ratchet teeth and no more.

3. A dose counter as claimed in claim 1, wherein the pawl is mounted on a resilient support.

4. A dose counter as claimed in claim 3, wherein the resilient support is a resilient flange incorporated into the body of the dose counter.

5. A dose counter as claimed in claim 1, further comprising a control surface to regulate the position of engagement and disengagement between the driver and the wheel.

6. A dose counter as claimed in claim 1, wherein the actuator is operable by linear displacement from a first position to a second position and back to the first position and wherein movement of the rotary gear occurs either during the displacement of the actuator from the first position to the second position or during the displacement of the actuator from the second position to the first position.

7. A dose counter as claimed in claim 1, wherein the actuator comprises a spring-loaded plunger, the plunger being depressible against a return force of a spring of the spring-loaded plunger when the actuator is caused to deliver a dose of medicament.

8. A dose counter as claimed in claim 1, wherein the driver comprises a ratchet drive pawl.

9. A dose counter as claimed in claim 8, wherein the ratchet drive pawl is in the form of a straddle drive in which an element that engages the ratchet teeth of the wheel is supported between a pair of spaced apart support arms.

10. A dose counter as claimed in claim 1, wherein the display is an elongate counter tape on which a dose count is printed or written.

11. A dose counter as claimed in claim 10, wherein the counter tape is located on an indexing spool and the dose counter further comprises a stock bobbin to receive the counter tape as the indexing spool is advanced in a step-wise fashion.

12. A dose counter as claimed in claim 1, wherein the actuator is adapted to engage with a rim of a medicament canister.

13. A dose counter as claimed in claim 1, wherein the wheel of the rotary gear has eight to fourteen ratchet teeth around a periphery of the rotary gear.

14. A dose counter as claimed in claim 13, wherein the wheel of the rotary gear has eleven ratchet teeth around its periphery.

15. A dose counter as claimed in claim 1, wherein the wheel of the rotary gear has a radius defined as the distance from the centre of the wheel to a tip of the teeth of 2.80+−0.05 mm and eleven ratchet teeth around its periphery, and the pawl comprises two ratchet teeth and no more which have a radial spacing of about 0.6 mm.

16. A metered dose inhaler comprising a medicament canister, an actuator body for receiving the canister and having a medicament delivery outlet, and the dose counter as claimed in claim 1.

17. A metered dose inhaler according to claim 16 wherein the actuator body comprises a smooth rounded sump.

18. The use of a dose counter for preventing miscounting in a metered dose inhaler, the dose counter comprising: an actuator; a rotary gear; a driver for driving the rotary gear in a step-wise fashion in response to displacement of the actuator, the rotary gear comprising a wheel mounted on a spindle which wheel having a plurality of ratchet teeth around its periphery; a pawl to prevent reverse rotation of the rotary gear; and a display coupled to the rotary gear, the display having a visible array of incrementing integers on a surface thereof indexable by a single integer in response to each step of the step-wise rotary motion of the rotary gear; wherein the pawl comprises at least two ratchet teeth each for engaging with the ratchet teeth of the wheel to prevent reverse rotation of the rotary gear, the at least two ratchet teeth being radially spaced such that one of the at least two ratchet teeth of the pawl engages with the ratchet teeth of the wheel following each step of the step-wise rotary motion of the rotary gear.

19. The use of a dose counter for preventing undercounting in a metered dose inhaler, the dose counter comprising: an actuator; a rotary gear; a driver for driving the rotary gear in a step-wise fashion in response to displacement of the actuator, the rotary gear comprising a wheel mounted on a spindle which wheel having a plurality of ratchet teeth around its periphery; a pawl to prevent reverse rotation of the rotary gear; and a display coupled to the rotary gear, the display having a visible array of incrementing integers on a surface thereof indexable by a single integer in response to each step of the step-wise rotary motion of the rotary gear; wherein the pawl comprises at least two ratchet teeth each for engaging with the ratchet teeth of the wheel to prevent reverse rotation of the rotary gear, the at least two ratchet teeth being radially spaced such that one of the at least two ratchet teeth of the pawl engages with the ratchet teeth of the wheel following each step of the step-wise rotary motion of the rotary gear.

* * * * *